United States Patent [19]

Ortega et al.

[11] Patent Number: 5,122,595

[45] Date of Patent: Jun. 16, 1992

[54] SAF POLYPEPTIDE GENE CODING THEREFOR, AND SAF PROMOTER

[75] Inventors: Antonio D. Ortega, Benacazon; Jose A. Gil, Leon; Tomas V. Garcia, Leon; Juan F. Martin, Leon, all of Spain

[73] Assignee: Applied Research Systems ARS Holding N.V., Curacao, Netherlands Antilles

[21] Appl. No.: 354,265

[22] Filed: May 19, 1989

[51] Int. Cl.[5] .................... C07K 13/00; C07K 15/00; C12N 15/31
[52] U.S. Cl. .................................. 530/350; 536/27; 435/6; 435/69.1; 435/71.2; 435/91; 435/169; 435/172.1; 435/172.3; 435/252.3; 435/252.35; 435/320.1; 935/6; 935/9; 935/22; 935/29; 935/59; 935/60; 935/61; 935/66; 935/72; 935/75
[58] Field of Search ............. 530/350; 536/27; 435/6, 435/69.1, 71.2, 91.169, 172.1, 172.3, 252.3, 252.35, 320.1; 935/6, 9, 22, 29, 59, 60, 61, 66, 72, 75

[56] References Cited

PUBLICATIONS

Horinouchi et al., 1983, J. Bacteriol., vol. 155(31):1238–1248.

Primary Examiner—Richard C. Peet
Attorney, Agent, or Firm—Browdy and Neimark

[57] ABSTRACT

The cloning and characterization of a newly isolated gene, referred to as saf (secondary metabolism activation factor) is disclosed. This gene encodes a new amino acid polypeptide, referred to as the SAF polypeptide, which directly or indirectly modulates the expression of extracellular enzymes in Steptomyces. DNA units or fragments which encode the SAF polypeptide are also disclosed, as are vectors containing said DNA, host organisms transformed with such vectors, and processes for preparing extracellular enzymes or heterologous polypeptides by culturing such host organisms.

2 Claims, 10 Drawing Sheets 1 2 3 4 5 6 7

1 2 3 4 5 6 7

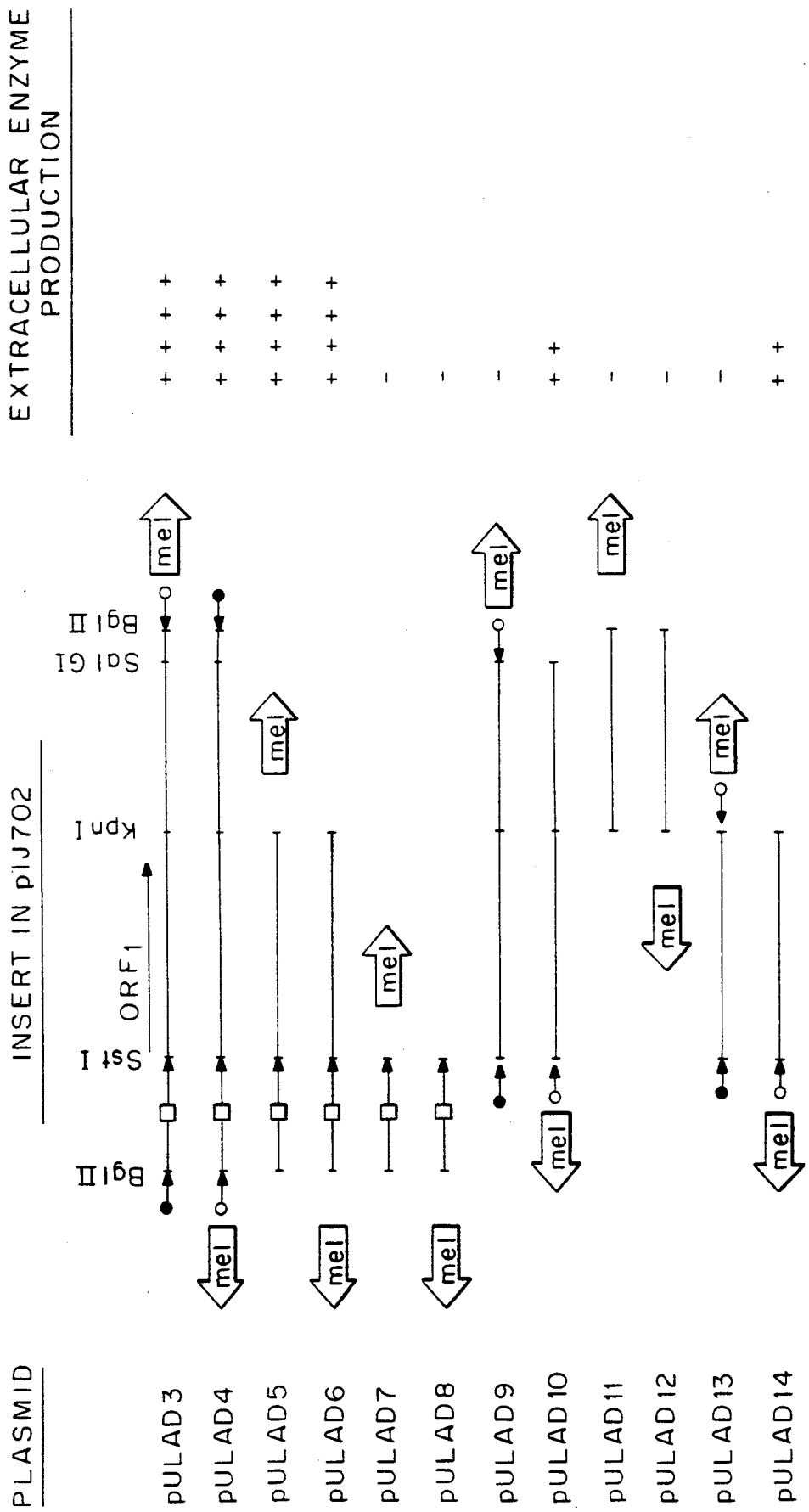

FIG.6A

```
BglII
AGATCTCCTCGTCCCACCGGCTGTCGAAGCTCCGCCTACAGGCCATCGACTTCGAC         59

CGGGGCGAAGTAGGAAGCGGGCGACAAAACGGGGAGGGGCGAAACGGTGGTCCGT        118

TTCCCGCCCCTGCCCGTAGGCCGTGCCGGTCCCGCCGGTGCGCGTTCAGCCCGCCG        177

Sst
         ATG TGC TCG GCC GTC GTC GCG GCC GTG AGC               215
CCGCT    Met Cys Ser Ala Val Val Ala Ala Val Ser

I
TCG ATG TCC CGC CGT CGC CGC CGG GCC AGC GCC ACC CGG CGC TCC      260
Ser Met Ser Arg Arg Arg Arg Arg Ala Ser Ala Thr Arg Arg Ser

GCT GCG GTG AGC CCG CCC CAC ACT CCG TAC GGC TCG GGC TGC ATC      305
Ala Ala Val Ser Pro Pro His Thr Pro Tyr Gly Ser Gly Cys Ile
```

FIG.6B

```
AGC GCG TGC TCC TGG CAC TCC ACC ATC ACC GGA CAC CGG GCA CAG    350
Ser Ala Cys Ser Trp His Ser Thr Ile Thr Gly His Arg Ala Gln

ACC CGC TTG GCC GCC CTC TCG CGG GCC AGC CGG GCG GCG GTC GGC    395
Thr Arg Leu Ala Ala Leu Ser Arg Ala Ser Arg Ala Ala Val Gly

TCC TTC GAC GGG GCG AAG AAC AGG CCG GCC TCG CGG CGG CAG        440
Ser Phe Asp Gly Ala Lys Asn Arg Pro Ala Ser Arg Arg Gln

GCC GCA TCG GAA TGC CAG GGG CCC GCG TCG TCC CGT GCG GGG        485
Ala Ala Ser Glu Cys Gln Gly Pro Ala Ser Ser Arg Ala Gly

GTC CGC TGG GCC GGA ACG GCG GCG AAC GGC AGA GGC TGA            524
Val Arg Trp Ala Gly Thr Ala Ala Asn Gly Arg Gly ter

TGCGGGGGGTTGCAGCACGGTCTACTCCTGACGACGGCTACGGCTTCGCGGAGGATGAGTC 583
```

FIG.6C

```
GATGCAGCTCTCCCTACCCGCTGTGCGTAAGCACGGAGCGCCACCAGCGCCG     642
         KpnI
GGGTACCGGAATGCGCCCCGGCCCCGGGCCTTTTGGCCGATTACCGGAGGTCGCCGCCCCGC     701
                        ←------→
CGTATACCGTGGGCACCACCGTATTCAGTGGCCGAGGTGTTTGCGCAGCCGCTGCTGGA     760

GGTCCGCCACGAACTTGCCCCGCCTTCGGCCTGCCTTCCACGCTGCCGAACACGGAATAG     819

CCGTTGACCACGACGACCGGGTGCTTCCGGGTCCGCCGATTCGAGCGTCCGCACGTCGAA     878
                                                        S
GGTGCCGAAGACGCCCGTGCCGCAGGGAAATGTTCTCCGGCACCCGGACGT     937
  StI
CGACGCTGCCGAAGATGGACGTCGCATTGATAACGGTGAGGCGTTGCCCGAAAAGGCT     996
   BglII
TCGGTGAGATCT      1008
```

| | | | | | | | | | | | | | | | | | | | | |
|---|---|---|---|---|---|---|---|---|---|---|---|---|---|---|---|---|---|---|---|---|
| λCI | Gln | Glu | Ser | Val | Ala | Asp | Lys | Met | Gly | Met | Gly | Gln | Ser | Gly | Val | Gly | Ala | Leu | | |
| λCro | Gln | Thr | Lys | Thr | Ala | Lys | Asp | Leu | Gly | Val | Tyr | Gln | Ser | Ala | Ile | Asn | Lys | Ala | | |
| LacI | Leu | Tyr | Asp | Val | Ala | Glu | Tyr | Ala | Gly | Val | Ser | Tyr | Gln | Thr | Val | Ser | Arg | Val | | |
| Lex | Ala | Ala | Glu | Ile | Ala | Gln | Arg | Leu | Gly | Phe | Arg | Ser | Pro | Asn | Ala | Ala | Glu | Glu | | |
| Lex R | Arg | Ala | Glu | Ile | Ala | Gln | Arg | Leu | Gly | Phe | Arg | Ser | Pro | Asn | Ala | Ala | Glu | Glu | | |
| P22Rep | Gln | Ala | Ala | Leu | Gly | Lys | Met | Val | Gly | Val | Ser | Asn | Val | Ala | Ile | Ser | Gln | Trp | | |
| CAP | Arg | Gln | Glu | Ile | Gly | Asn | Ile | Val | Gly | Cys | Ser | Arg | Glu | Thr | Val | Gly | Arg | Ile | | |
| Fnr | Arg | Gly | Asp | Ile | Gly | Asn | Tyr | Leu | Gly | Leu | Thr | Val | Glu | Thr | Ile | Ser | Arg | Leu | | |
| Saf | Arg | Ala | Ala | Val | Gly | Ser | Phe | Asp | Gly | Ala | Lys | Asn | Arg | Pro | Ala | Ser | Ser | Arg | | |
| AfsB$_a$ | Gln | Arg | Arg | Tyr | Ala | Glu | Gly | Lys | Gly | Leu | Phe | His | Gln | Ala | Ile | Ala | Gly | Phe | | |
| AfsB$_b$ | Glu | Gln | His | Asp | Ala | Gln | Glu | Val | Gly | Glu | Val | Arg | Ala | Leu | Leu | Ala | Arg | Ser | | |

FIG. 7

SAF POLYPEPTIDE GENE CODING THEREFOR, AND SAF PROMOTER

The invention is in the field of biotechnology. More particularly, it relates to a new polypeptide increasing production of extracellular enzymes. DNA that codes for the polypeptide, a recombinant vector that includes the DNA, and a host organism transformed with the recombinant vector that includes the DNA encoding the polypeptide. Furthermore the invention is directed to the promoter sequence of the gene encoding the new polypeptide.

BACKGROUND ART

The Streptomyces are well known producers of a variety of extracellular enzymes including proteases, phosphatases, xylanases, cellulases, amylases, lipases and nucleases.

In addition members of the genus Streptomyces produce a large number of antibiotics, pigments and other secondary metabolites and have a complex pattern of differentiation resulting in the formation of spores. In batch cultures of Streptomyces there is, usually a coincidence in the production of extracellular enzymes and the onset of antibiotic production and pigment biosynthesis and sporulation. All these processes are repressed by nutritional conditions favoring high growth rates and are der pressed by starvation of P, C or N sources. It is likely that enzyme secretion, formation of secondary metabolites and differentiation are completely independent but respond to similar triggering mechanisms.

Several genes of Streptomyces encoding extracellular enzymes have been cloned. These include agarase from *Streptomyces coelicolor*, endoglycosidase H from *Streptomyces plicatus*, xylanase from *Streptomyces lividans*, alfa-amylase from *Streptomyces hygroscopicus*, cellulase from *Strep. spA2*, beta-galactosidase from *Strep. lividans* and beta-lactamases from *Strep. cacaoi, badius* and *fradiae*.

However the regulatory mechanism which control expression of these genes are virtually unknown. In addition to specific regulatory mechanisms such as induction of amylase by dextrins or maltotriose and carbon metabolite regulation of amylase or agarase, general mechanisms of derepression of several extracellular enzymes are likely to occur since simultaneous production of several polymeric-substrate degrading enzymes has been observed in Streptomyces following a nutritional down-shift. Such transacting regulatory genes have been found in *Bacillus subtilis* (J. BACTERIOL. 169:324-333,1987), *Bacillus natto* (J. BACTERIOL. 166:20-28,1986), and *Bacillus licheniformis*.

Positive regulatory genes affecting enzyme synthesis and/or secretion might be cloned by searching for increased secretion of extracellular enzymes in a poor secretory strain such as *S.livida*

OBJECT OF THE INVENTION

A principal object of this invention is to provide the cloning and characterization of a newly isolated gene, hereinafter referred to as saf (secondary metabolism activation factor) gene, encoding a new amino acid polypeptide (hereinafter referred to as SAF polypeptide). The SAF polypeptide modulates directly or indirectly expression of the genes for extracellular enzymes in Streptomyces by interacting with the control region of the structural genes for the extracellular enzymes.

A second aspect of the invention is DNA units or fragments comprising nucleotide sequences that upon expression encode the above described SAF polypeptide.

A third aspect of the invention is cloning vehicles (vectors) that include the above described DNA.

A fourth aspect of the invention is host organisms or cells transformed with the above described cloning vehicles thereby resulting increased production of extracellular enzymes or of a desired heterologous polypeptide.

A fifth aspect of the invention is a process for the preparation of extracellular enzymes or of a desired polypeptide by culturing a transformed host organism according to the present invention and recovering the product from the culture broth.

Still another aspect of the invention is the promoter of the saf gene.

These and other objects of the invention will be described in more detail in the further specification.

SUMMARY OF THE INVENTION

A DNA fragment from *Streptomyces griseus* ATCC 10137 has been isolated that encodes a gene saf (secondary metabolism activation factor) which is involved in a common control mechanism for at least five extracellular enzymes in *S. lividans* and *S. coelicolor*. The saf gene is present in all Streptomyces tested which suggests that this gene must have an important role in metabolism. Indeed, a DNA fragment containing a similar gene to saf has been cloned by us from *Streptomyces griseus IMRU* 3570, the candicidin producer strain. In some Streptomyces, e. g. *S. lividans* and *S. lactamdurans*, the hybridization pattern suggests that the saf gene is present in several copies in the chromosomal DNA.

This is the first example of a gene involved in production of extracellular enzymes and sporulation in Streptomyces.

The saf gene encodes a polypeptide of 113 amino acids (the SAF polypeptide); in vitro transcription-translation studies in *E. coli* showed that a protein of the correct size, about 15000 dalton is formed. The SAF polypeptide has a strong positive charge (18 positively charged amino acids) and does not show composition typical of a peptide leader or a transmembrane protein and therefore, a direct effect on protein excretion appears to be unlikely. The positively charged protein may easily interact with DNA. In fact a DNA-binding domain typical of several regulatory proteins (ANN. REV. BIOCHEM. 53: 293-321, 1984) is observed in the SAF polypeptide.

The SAF polypeptide has a pleiotropic effect, i.e. an effect affecting more than one pathway, on extracellular enzymes, on pigment production and on differentiation. In accordance with the invention, an increased production of endogenous (extracellular) proteins is achieved.

Broadly the saf gene and corresponding polypeptide could be used to increase expression in Streptomyces of selected heterologous protein by inserting the gene coding for the desired protein into a suitable cleavage site of the gene coding for the extracellular enzyme or a part thereof, transforming a Streptomyces host containing the saf gene with the recombined gene, and culturing the transformed bacteria to excrete the selected protein or portion thereof.

Pleiotropic genes affecting biosynthesis of antibiotics and differentiation in Streptomyces have been reported. A gene afsB which positively controls the production of A-factor, actinorhodin and prodigiosin in *Streptomyces coelicolor* and *Streptomyces lividans* was cloned from *S. coelicolor* A3(2) (Horinouchi et al., J. BACTERIOL. 155:1238-1248, 1983).

The saf gene is different from the afsB and in fact they have opposite effects on production of actinorhodin. They have in common that they have an amino acid sequence typical of DNA-binding proteins. Both afsB and saf genes have promoters without the $-10$ and $-35$ consensus sequences and are bounded by potential translational regulatory signals and by strong stem and loop structures that may act as transcriptional terminators (Horinouchi et al. J. BACTERIOL. 168:257-269, 1986). If the transcription forms a very stable loop, binding of the ribosomes will be precluded. Such atenuation-like mechanisms of control of gene expression have been found to modulate control of antibiotic-resistance genes in Streptomyces (Horinouchi et al. PROC. NATL. ACAD. SCI. USA 77:7079-7083, 1980). Since the saf gene might be considered as a "master" gene which switches on a variety of genes for enzyme excretion, its expression is probably tightly controlled in the cell. The enzymes stimulated by the saf gene are all involved in the degradation of complex polymers and therefore we speculate that this gene is part of a global regulatory system involved in the search for alternative nutrient sources, as suggested also in Bacillus (Henner at al. J. BACTERIOL. 170:296-300, 1988).

BRIEF DESCRIPTION OF THE DRAWINGS

FIG 5: Trimming down of the saf gene. The 1 kb BglII fragment of pULAD3 was used as starting material. Extracellular enzyme production for all the plasmid constructions was measured on solid media plates as indicated in the description: −, wild type producer; ++, +++ and ++++ indicate different rates of hyperproduction.

Short open arrows indicate the localization and direction of the transcription of the tyrosinase gene (mel) in plasmid pIJ702. Closed circles ● indicate the mel gene promoter; open circles O represent a putative clockwise promoter activity in pIJ702 and open squares □ indicate the saf promoter. The direction of transcription is shown by arrows. The ORF1 corresponds to the saf reading frame deduced from nucleotide sequence data (see FIG. 6).

FIG. 6: Nucleotide sequence of the 1 kb BglII fragment of pULAD3 and deduced amino acid sequence of the saf gene product. The second putative ATG initiation condon is underlined. Inverted complementary repeat sequences are shown by convergent arrows. The wavy line indicates the amino acid sequence similar to DNA-binding domains of known DNA-binding proteins. The relevant restriction sites are shown. The nucleotides are numbered starting with the BglII site (numbers on the right).

FIG. 7: Comparison of a region from the deduced amino acid sequence of the saf gene product with DNA-binding domains in known DNA-binding proteins. Data were taken from Pabo and Sauer (Pabo et al. ANN. REV. BIOCHEM. 53:293-321, 1984) and Horinouchi and Beppu (Horinouchi et al. GENETIC OF INDUSTRIAL MICROORGANISMS. p.41 Pliva, Zagreb, Yugoslavia, 1986)

Figure 8:
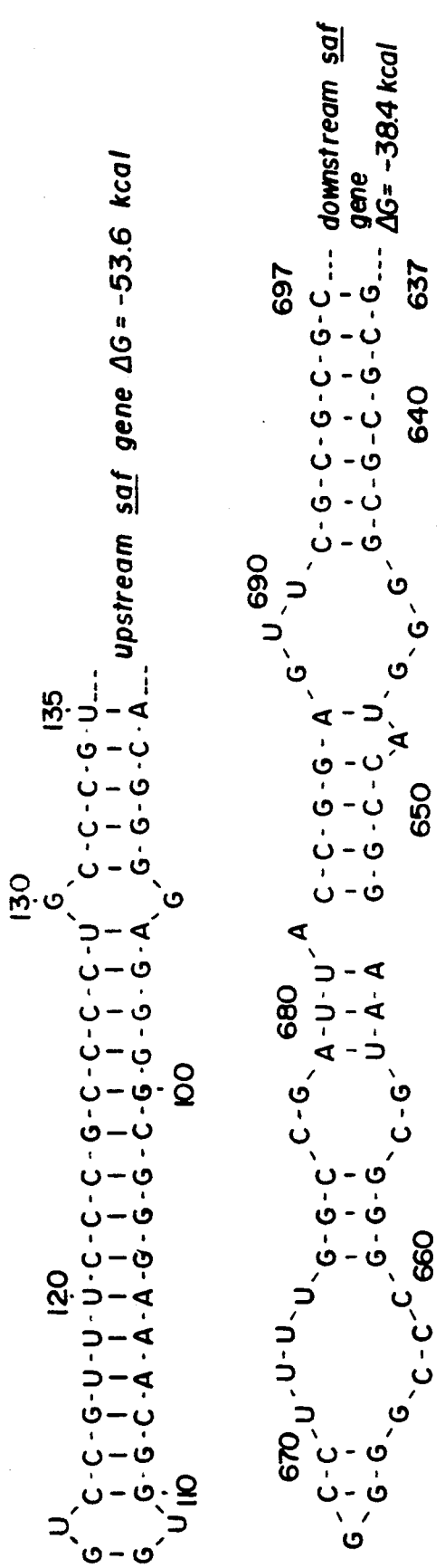

FIG. 8: Repeated nucleotide sequences "upstream" and "downstream" of the saf gene.

Figure 9:
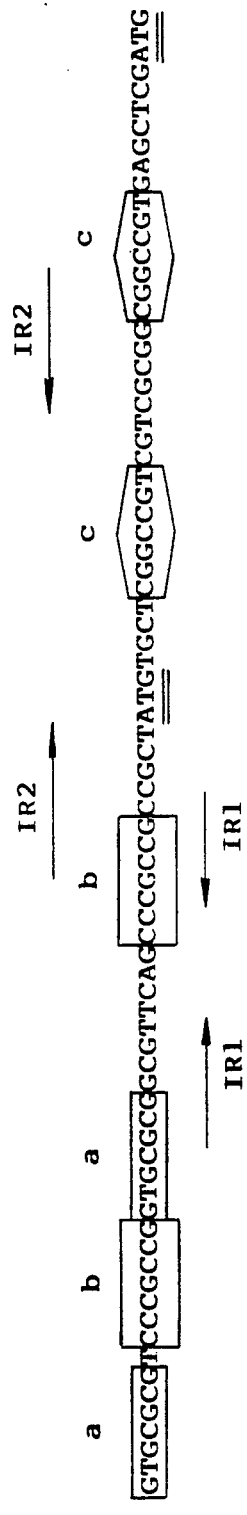

FIG. 9: Repeated groups of nucleotides present in the saf gene.

Figure 10:
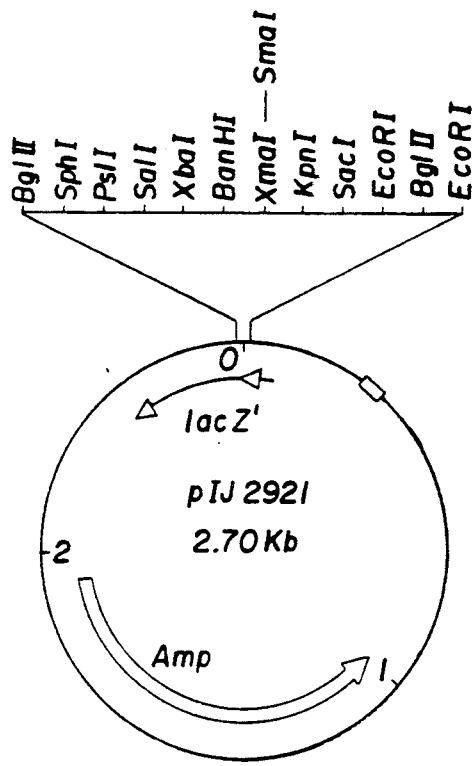

FIG. 10: Plasmid pIJ2921.

DESCRIPTION OF PREFERRED EMBODIMENTS

The work described herein was performed employing the following materials and methods.

Bacterial strains and plasmids. The Streptomyces and *E.coli* strains used in this study are listed in Table 1. Plasmids and phages are in Table 2.

Media and culture conditions. Streptomyces strains were grown in R2YE, minimal medium (MM), TSB (Difco) or YEME supplemented with 34% sucrose and 5 mM MgCl$_2$ (Hopwood et al. Genetic manipulation of Streptomyces. A LABORATORY MANUAL. THE JOHN INNES FOUNDATION, NORWICH, U.K.,1985). Streptomyces strains were grown in triple baffled flasks at 28° C. in a rotary shaker with an agitation of 220 rpm.

*E.coli* strains were grown in Luria Broth (LB) (Miller et al. EXPERIMENTS IN MOLECULAR GENETICS. p.433. Cold Spring Harbor Laboratories, New York, 1972) o Luria Agar (LA) at 37° C.

Enzyme assays in plates. Alkaline phosphatase (AP) assays for Streptomyces were carried out in PRMM medium (MM) without glucose and containing a reduced level [1mM] of phosphate supplemented with 30 mcg/ml of 5-bromo-4-chloro-3-indolylphosphate-p-toluidine (XP). Colonies producing AP were blue and those unable to produce it were white. For *E.coli*, B-XP medium was used (containing per liter: 10 g bactopectone, 12 g Trisma-base, 10 g NaCl, 20 g Difco agar, pH 7.5 and 40 mcg/ml of XP).

Amylase activity of Streptomyces colonies was assayed on MM (without glucose) supplemented with 1% starch. After 3 days of growth, the plates were exposed to iodine vapor. Zones of clearing around the colonies are due to starch degradation. Lipase activity was measured by growing the Streptomyces in MM supplemented with 2% (w/v) olive oil, 0.5% (w/v) Tween 80 and 0.5% (w/v) Tween 20. After 3 days of growth the plates were flooded with 1 ml of 1M CaCl$_2$. The lipase production was observed as a precipitate of Ca$^{2+}$-fatty acid complex (Odera et al. FERMENT. TECHNOL. 64:363-371, 1986). Protease activity was assayed in MM (without glucose) supplemented with 0.5% casein and 10 mM CaCl$_2$. The enzyme activity was detected as zones of clearing around the colonies.

Agarase activity of S.coelicolor was assayed in MM without glucose by flooding the plates with Gram's iodine solution. Beta-galactosidase activity was observed as a blue color of the colonies growing on MM without glucose, and supplemented with X-gal (36 mcg/ml) and IPTG (10 mcg/ml).

DNA isolation: Total DNA from Streptomyces was prepared as described by Hopwood et al. (Hopwood et al. A LABORATORY MANUAL, The John Innes Foundation, Norwich, U.K., 1985). Plasmid DNA from Streptomyces or E.coli was isolated following the method of Kieser (Kieser et al. PLASMID 12:19–36, 1984).

Cloning procedures: Ten mcg of S.griseus ATCC 10137 chromosomal DNA and 0.5% mcg of pIJ702 were totally digested with BglII, and ligated for 12 h at 14° C. using T4 DNA ligase. The ligation mixture was used directly for transformation. Subcloning of DNA fragments was carried out by digesting 1-2 mcg of plasmid DNA with adequate restriction enzyme(s) and the reaction products were separated by gel electrophoresis in low melting point agarose (LMPA). The required DNA bands were extracted using the CTAB-assisted method (Langridge et al. ANAL. BIOCHEM. 103:264–271, 1980).

Transformation methods: Streptomyces strains were transformed as described by Hopwood et al. (Hopwood et al. A Laboratory Mannual, The John Innes Foundation, Norwich, U.K., 1985). After transformation, protoplasts were plated on R2YE medium, and allowed to regenerate for 15–20 h at 30° C. Then, 1 ml of an aqueous solution of thiostrepton (300 mcg/ml) was poured over the plates, dried for 1 or 2 h and incubated for 2 or 3 days more. Transformants were replicated to PRMM medium containing thiostrepton (50 mcg/ml) and XP (30 mcg/ml).

Transformation of E.coli was done according to Cohen et al. (PROC. NATL. ACAD. SCI. USA 69:2110–2114, 1972). Transformants were selected on plates containing ampicillin (200 mcg/ml). When required, X-gal (36 mcg/ml) and IPTG (10 mcg/ml) were added to LA plates.

Hybridization studies: Transfer of DNA from agarose gels to nitrocellulose filters and hybridizations were carried out as described by Hopwood et al. (A Laboratory Mannual, The John Innes Foundation, Norwich, U.K., 1985). The 7.2 Kb BglII fragment from plasmid pULAD1 and the 1 Kb BglII fragment from plasmid pULAD3 were used as probes. Hybridizations were performed at 70° C. for 24 h. The filters were washed twice for 30 min in 2×SSC, 0.1% SDS and then twice again for 30 min in 0.2×SSC, 0.1% at 70° C.

Nucleotide sequence analysis: The nucleotide sequence was determined by the chain termination method of Sanger et al. (PROC. NATL. ACAD. SCI. USA 74:5463:5467, 1977). The DNA fragments were subcloned into M13mp10 and M13mp11 to obtain the insert in either orientation. Ligation mixtures were transfected into competent E.coli JM103 cells and white plaques were screened for selection of inserts. The sequencing was performed in both strands using Amersham International plc. (U.K.) and Sequenase (United States Biochemical Corporation, USA) kits. All the fragments were sequenced using dGTP, but dITP was used instead of dGTP when needed. Reaction mixtures were separated on 6% or 8% polyacrylamide sequencing gels which were then exposed to X-ray film for autoradiography.

Promoter cloning: Fragments with transcription initiation activity were selected by using the multicopy promoter-probe plasmid pIJ486 (Ward et al. MOL. GEN. GENET. 203:468–478, 1986). Kanamycin (Km) resistant transformants were isolated by replication of colonies to MM containing 15 mcg/ml of Km.

In vitro transcription-translation. Plamids pU-LAD300 and pUC19 were transcribed and translated using the prokaryotic DNA directed translation kit from Amershan International plc. L-($^{35}$S) methionine was used as radioactive label. 12.5% po .crylamide gels containing sodium dodecyl sulphate were used to analyze the labelled proteins.

MODES OF CARRYING OUT THE INVENTION

The following detailed description will illustrate the invention:

Alkaline phosphatase production by different Streptomyces

The alkaline phosphatase production in several solid media of ten different Streptomyces strains (listed in Table 1) was assayed. S.griseus IMRU 3570 and S.griseus ATCC. 10137 were the best producers in all the media assayed. The best solid medium for alkaline phosphatase production was PRMM (containing 30 mcg/ml XP). In this medium S.griseus IMRU 3570 and S.griseus ATCC. 10137 showed a deep blue color after 48 h of growth. S.lividans 1326 and S.coelicolor JI 2280 were poor alkaline phosphatase producers: after 90 h of growth on PRMM containing XP only a weak blue color can be observed.

Cloning of a gene involved in alkaline phosphatase production

Figure 1:
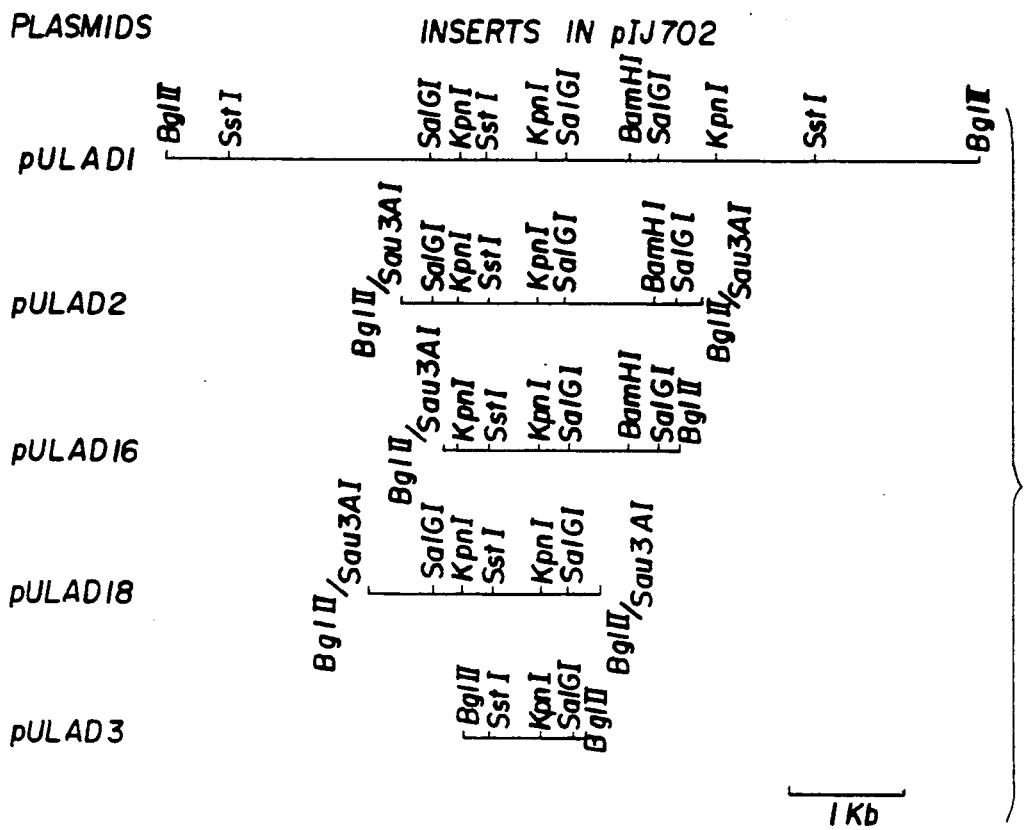
FIG. 1: Restriction maps of chromosomal DNA fragments from *S. griseus* ATCC 10137 clones in the BglII site of pIJ702 that carry the genetic determinant for alkaline phosphatase hyperproduction.

Total DNA from S.griseus ATCC. 10137 was digested with BglII, ligated to BglII-digested pIJ702 and the ligation mixture introduced by transformation into S.lividans 1326 protoplasts. The transformants were replicated to PRMM containing thiostrepton (50 mcg/ml) and XP (30 mcg/ml). One deep blue colony was found among 2,800 melanine negative transformants of S.lividans. The deep blue colony contained a pIJ702 derivative carrying a 7.2 kb BglII insert which was named pULAD1 (FIG. 1).

Plasmid pULAD1 was unstable in S.lividans and upon retransformation gave rise to white and blue colonies. All the blue colonies contained the original pULAD1 and the white ones contained deleted forms of pULAD1 that were no longer studied. Since the instability might be caused by the large size of the insert in a plasmid such as pIJ702 which is known to have a certain instability, the 7.2 kb insert was subcloned into the 5 kb BglII fragment of plasmid pIJ699 (Kieser et al. GENE 65:83–91, 1988). Two plasmids, pULAD100 and pULAD101 were obtained with the insert in opposite orientation. Both plasmids were stable and the gene was expressed in both orientations in S.lividans.

Localization of the Saf gene

The 7.2 Kb BglII fragment was partially digested with Sau3AI, and ligated to BglII-digested pIJ702. The ligation mixture was transformed into S.lividans protoplasts and transformants were replicated to PRMM containing XP. Plasmid DNA was isolated from several blue colonies. Four small plasmids pU-LAD2, pULAD3, pULAD16 and pULAD18 carrying the determinant for alkaline phosphatase production were studied in detail; they were stable, retransformed S.lividans protoplasts, and carried inserts of 2.4, 1, 2.1 and 1.9 Kb (FIG. 1 respectively). The plasmid pU-LAD3 has the smallest insert (1 Kb) which can be rescued with BglII. When introduced into S.lividans, pU-LAD3 (deposition number I-859 on 19.05.89 with CNCM (Collection Nationale de Cultures de Mcroorganisms, 28 rue du Docteur Roux, F75724 Paris Cedex 15, France) under the Budapest Treaty and Rule 28 EPC) increased alkaline phosphatase production like pULAD1.

Hybridization with chromosomal DNA of several Streptomyces

Total DNA from S.griseus ATCC 10137 digested with BamHI or BglII were hybridized to the 7.2 Kb BglII fragment from pULAD1 labelled by nick translation with ($^{32}$p) dCTP. A 7.2 Kb BglII fragment homologous to the probe was present in S.griseus ATCC 10137 DNA digested with BglII, as expected. There was an internal BamHI site in the fragment, that resulted in two clear hybridization bands (of 7.9 Kb and 9.4 Kb) when total DNA was digested with BamHI.

Figure 2A:
FIG. 2: Southern hybridization analysis of homology between the 1 kb BglII fragment of pULAD3 and genomic DNA of other Streptomyces species. (A) DNA fragments generated by BamHI digestion of genomic DNAs (Lanes 2 to 7). (B) Hybridization of DNAs shown in panel A, with the 1 kb fragment as the probe. Lanes: 1, HindIII digest of DNA giving fragments of 23, 9.59, 6.68, 4.29, 2.28, 1.94 and 0.58 kb; 2, *S.lactamdurans*; 3, *S.acrimycini*; 4, *S.coelicolor* 1157; 5, *S.griseus* 2212; 6, *S.griseus* 3570; 7, *S.lividans* 1326.
Figure 2B:

To study if the same gene was present in other Streptomyces, total DNA from S.acrimycini, S.coelicolor 1157, S.griseus 2212, S.griseus 3570, S.lividans 1326 and S.lactamdurans NRRL 3802 were digested with BamHI and hybridized with the 1 Kb BglII fragment of pULAD3 as a probe. Hybridization with a 9.5 Kb common band was observed in the first four strains of Streptomyces cited above, whereas 4 and 5 weak hybridization bands were observed in the DNA of S.lividans and S.lactamdurans respectively (FIG. 2). In addition, hybridization was also observed with the DNA of S.albus G, S.coelicolor JI 2280, S.clavuligerus NRRL 3585 and S.fradiae ATCC 10475. No further attempts were made to characterize the hybridizing bands.

Lack of complementation of E.coli pho-mutants

Complementation of the E.coli phoA mutants E15 and AW1046 was tried to check if we had cloned the alkaline phosphatase structural gene from S.griseus ATCC 10137. The 7.2 Kb BglII fragment from pU-LAD1 and the 1Kb BglII fragment from pULAD3 were subcloned separately in both orientations in BamHI-digested pUC19. All these plasmid constructions were verified in E.coli JM103 cells and then used to transform E.coli E15 (Sarthy et al. J. BACTERIOL 145:288-292, 1981) and E.coli AW1046. No blue colonies in B-XP were found suggesting that the complete structural gene for alkaline phosphates is not present in the 7.2 Kb fragment of S.griseus or that it is not expressed in E.coli. The structural gene for alkaline phosphatase (phoA) of Bacillus licheniformis (Hullett, F. M. J. BACTERIOL. 158:978-982, 1984) did not hybridize with the cloned 1 Kb fragment (data not shown).

In addition, the phoB (regulatory) E.coli mutant H2 (Kreuzer et al. GENETICS 81:459-468, 1975) was not complemented by either the 1 kb Bg'lII fragment of pULAD3 or the 7.2 BglII fragment of pULAD1.

Overproduction of other extracellular enzymes

Figure 3A:
FIG 3: Assays on Petri dishes of protease (A), amylase (B) and lipase (C) activities of *S.lividans* transformed with pIJ702 (left) and *S.lividans* transformed with pULAD3 (right).
Figure 3B:
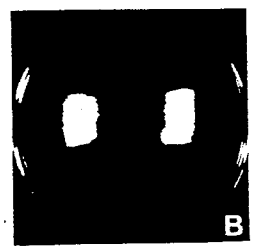
Figure 3C:

When pULAD3 was used to retransform S.lividans protoplasts a clear delayed pigmentation and sporulation was observed. These pleiotropic effects prompted us to study the role of this gene in protein secretion or in control of gene expression. As shown in FIG. 3, several extracellular enzymes including amylase, protease and lipase were overproduced by S.lividans transformed with pULAD3. The β-galactosidase production was also increased and its production started about 24-30 h earlier than in untransformed S.lividans or S.lividans transformed with pIJ702. S.coelicolor JI2280 transformed with pULAD3 also overproduced alkaline phosphatase, β-galactosidase, protease, amylase and lipase but the agarase production was not significantly increased. The actinorhodin synthesis of S.coelicolor clones transformed with pULAD3 was delayed by more than 30 hours with respect to untransformed S.coelicolor. Due to the pleiotropic effects of the cloned gene on extracellular enzymes, on pigment production and on differentiation this gene was named saf (secondary metabolism activation factor).

Gene dosage effect

The copy number of pIJ702 is estimated to be 100 to 200 per chromosome. Although the exact copy number of pULAD3 was not determined, the intensity of both pIJ702 and pULAD3 bands suggested a similar copy number.

Figure 4A:
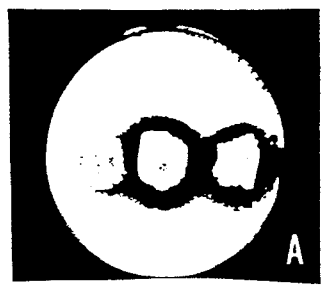
FIG 4: Gene dosage effect on the expression of the saf gene. Production of protease (A) and amylase (B) by *S.lividans* transformed with pIJ702 (left), *S.lividans* transformed with pULAD3 (middle) and *S.lividans* transformed with pULAD30 (right).
Figure 4B:
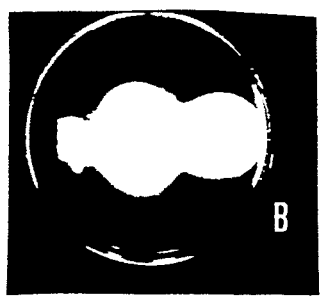

To study the gene dosage effect we subcloned the 1 kb BglII fragment of pULAD3 into the BamHI site of the low copy number plasmid pIJ61 (3 to 4 copies per cell) (Hopwood et al. A Laboratory Mannual. The John Innes Foundation, Norwich U.K.). This new plasmid was named pULAD30. FIG. 4 shows that the production of extracellular enzymes by S.lividans transformed with pULAD30 clearly decreased with respect to S.lividans carrying pULAD3. In addition, S.lividans carrying pULAD30 showed a similar pigment production and sporulation pattern than untransformed S.lividans.

Expression in E.coli and trimming down of the gene

Although pho mutants of E.coli were not complemented by the saf gene we observed that the 1 kb BglII insert of pULAD3, when subcloned in one direction in pUC19 (plasmid named pULAD300) was expressed in E.coli causing abnormal morphology when grown on solid media, but it was not expressed when inserted in opposite orientation (plasmid pULAD301). Plasmid pULAD300 contains the ORF (see below) downstream from the lacZ promoter. These results suggest that the saf gene is expressed in E.coli from the lacZ promoter present in pUC19.

In-vitro transcription-translation in E.coli assays (with pULAD300) were carried out and the products of the reaction were loaded in a 12.5% polyacrylamide gel. A band of MW 15000 was present in the lane corresponding to pULAD300 which was absent in the control pUC19 lane.

To locate precisely the saf gene it was decided to continue the splitting of the 1 Kb fragment of plasmid pULAD300. In these trials there was exploited the existence of unique cut sites for restriction enzymes Sst I (nt 216), Kpn I (nt 648) and Sal GI (nt 936) within the 1 kb fragment. The different sub-fragments from the 1 kb insert of pULAD300 were cloned in a first step into pIJ2921, a derivative of pUC18 containing a modified polylinker flanked with BglII sites (see FIG. 10) and then rescued with BglII cohesive ends and cloned into BglII-digested pIJ702. Alkaline phosphatase, amylase and protease production was studied in Streptomyces lividans with all plasmids constructions. The results of these studies appear in outline form in FIG. 5 and the following conclusions have been extracted from their interpretation:

1. The 1 kb fragment contains the complete saf gene, including its own promoter, since it was expressed at a similar level in both orientations of plasmid pIJ702 (plasmid pULAD3 and pULAD4).
2. The saf gene seems to be located in the 648 nucleotides BglII-KpnI fragment (plasmids pULAD5 and pULAD6).
3. Fragment SstI-Kpn (432 nucleotide) seems to contain the genetic determinant for extracellular enzyme hyper-production, but appears to have lost its promoting region, since it was expressed only in one orientation (plasmid pULAD10 and pULAD14), but not on the opposing one (plasmid pULAD9 and pULAD13).
4. The 215 nucleotides fragment BglII-SstI contains the saf gene promoter region.
5. All the effects on extracellular enzymes and on differentiation were kept or lost together, indicating that a single genic product was responsible for the action on all the enzymes.
6. A surprising aspect was the lack of expression of fragment SstI-KpnI (saf gene without promoter), starting from the tyrosinase promoter of the mel-gene present in pIJ702, which nevertheless was expressed in the opposite direction (clockwise direction). This finding implied that there was a fragment with promoter activity located before gene mel, and at the BglII cloning site (Bernan et al., GENE 37:101-110, 1985). Although such finding has not been published, it has occasionally been mentioned by some authors (Gil and Hopwood, GENE 25:119-132,1983).

The possibility of a functional ORF in reverse direction (from KpnI -- SstI) was discarded, for several reasons:
A. Such ORF was not detected when the nucleotide sequence was analyzed.
B. If such ORF were to exist, it would be clear that it would have to carry its own promoter, since fragment BglII-KpnI (nt 1 to nt 648) was expressed in both directions (plasmids pULAD5 and pULAD6). It did not make sense then, that the KpnI -- SstI fragment which would carry the promoter in the KpnI zone could only express itself in one direction.
C. Expression in E.coli always took place when the promoter lacZ was in favor of (before) the proposed ORF, and never in the opposite direction.

Promoter activity of ORF1 upstream DNA fragment

In order to confirm the existence of a promoter in the BglII- - SstI fragment, as could be inferred from previous experiments, said fragment was subcloned in the probe vector for pIJ486 fragments (Ward et al. MOL. GEN. GENET. 203:468-478, 1986), which carries the gene that codifies for aminoglycoside phosphotransferase (neo), without its promoter. The expression of this gene made S.lividans resistant to kanamycin and neomycin. When the fragment was subcloned in pIJ486 (with the SstI end next to neo gene), plasmid pIJ484::216 was created. It was observed that S.lividans transformed with pIJ486::216 grows in MM with over 100 mcg/ml Km while S.lividans transformed with pIJ486 did not grow in MM supplemented with 5 mg/ml Km. These results indicated that such fragment had promoter activity and supported the proposed ORF.

Other considerations that were deduced from the nucleotide sequence and probable ORF, included:

1. Gene saf was surrounded by two regions with inverted and complementary repeated sequences, which could form in mRNA very stable bonds ($\Delta G = -38.4$ kcal, being gene saf, nt 637-697) (FIG.8).
2. The sequenced fragment contains a high G+C percentage, as is usual in Streptomyces genes.
3. Before gene saf, between ATG (nt 219) and the repeated upstream structures, there is a very interesting nucleotide region: there are three pairs of repeated nucleotides (each one with 7 nt) (FIG.9). It is very likely that this region, especially the promoter zone, plays a very important part in the regulation of gene saf expression.
4. It is worth mentioning that the SAF protein contains 18 net positive charges. From a hypothetical perspective, this could imply the existence of a much greater affinity for DNA. Even in the deduced amino acid sequence, a very similar region to the domains of DNA-linking proteins can be observed (Pabo and Sauer, 1984) (FIG.7).

Nucleotide sequence of the saf gene

The nucleotide sequence of the entire 1 kb BglII insert of pULAD3 was determined using plasmid pULAD300 as the starting material. Since M13mp10 and M13mp11 have no KpnI site, the fragments with KpnI ends were first subcloned into pUC19 and then rescued as EcoRI-HindIII fragments and introduced into mp10 and mp11 digested with EcoRI and HindIII.

The complete nucleotide sequence of the active region shows an ORF1 of 339 nucleotides which encodes the putative SAF polypeptide (FIG.6). There is only one possible open reading frame contained in the BglII-KpnI fragment starting with an ATG initiation codon at nt 183 and terminating with a TGA stop codon at nt 524 (ORF1 in FIGS.5 and 6). Since the SstI-KpnI insert, contained in plasmid pULAD14, showed a lower degree of activity than plasmids containing also the upstream region of the SstI site (pULAD3, pULAD4, pULAD4 and pULAD6) it is very likely that the ATG (nt 219) also in frame with the presumptive saf reading frame may act as the initiation codon in pULAD10 and pULAD14. No other alternative initiation triplets are possible since a TGA termination codon exists upstream of the first ATG.

A long inverted repeat region which may form a very stable stem and loop structure ($\Delta G = -53.6$ kcal) is present upstream of the saf gene, from nt 90 to nt 135. Another hyphenated inverted repeat sequence was observed downstream from the terminator triplet of ORF1, extending from nucleotides 637 to 697, ($\Delta G = -38.4$ kcal).

The saf gene has a high G+C content (76.3%) and a marked bias in codon usage. Codons with a G or C. in the third position are very frequent (90.3%) as described for other Streptomyces genes (Hopwood et al. Regulation of Gene Expression 25 years on, Cambridge University Press. p.251-276, 1986).

Promoter activity of the DNA fragment upstream of the ORF1

Since plasmids lacking the BglII-SstI fragment (from nt 1 to nt 216) were only expressed in one orientation (plasmids pULAD10 and pULAD14), but not in the opposite (plasmids pULAD9 and pULAD13), it seemed likely that the ORF1 promoter was located in that fragment. The presence of a transcription initiating sequence in this region was confirmed by subcloning this fragment into the promoter-probe plasmid pIJ486 (Ward et al. MOL. GEN. GENET. 203:468:478, 1986) which carried a promoterless aminoglycoside phosphotransferase gene (neo), expression of this gene confers kanamycin and neomycin resistance to S.lividans. The BglII-SstI fragment was subcloned into pIJ486 (the SstI end proximal to the neo gene) (plasmid named pIJ486::216). S.lividans transformed with pIJ486::216 was able to grow on MM containing more than 100 mcg/ml of km, whereas S.lividans carrying pIJ486 does not grow on MM with 5 mcg/ml of km. This result indicates that the BglII-SstI fragment has promoter activity. However no typical "consensus" −10 or −35 regions were identified by nucleotide homology with other promoters of Streptomyces (Hopwood et al. Regulation of Gene Expression 25 years on, Cambridge University Press. p. 251-276. 1986).

TABLE I

Bacterial Strains

| Designation | Relevant characteristics | Source of reference |
|---|---|---|
| S. griseus ATCC 10137 | wild type | ATCC |
| S. griseus JI 2212 | wild type | JI |
| S. griseus IMRU 3570 | wild type | IMRU |
| S. lividans JI 1326 | wild type | JI |
| S. acrimycini JI 2236 | wild type | JI |
| S. coelicolor JI 2280 | CysE24, PabA1, strI | JI |
| S. coelicolor JI 1157 | wild type | JI |
| S. clavuligerus NRRL 3585 | wild type | NRRL |
| S. lactamdurans NRRL 3802 | wild type | NRRL |
| S. albus G | wild type | JI |
| E. coli E15 | phoA8 | CGSC |
| E. coli AW1046 | PhoA, phoC, tsX::tn5, leu, Kan$^R$ | 1 |
| E. coli H2 (E. coli CGSC 5259) | phoB52, pho-35 | CGSC |
| E. coli JM103 | proAB, lacZΔM15 | 2 |

JI : Collection of microorganisms of the John Innes Institute. Coleny Lane, Worwich NR4 UH, United Kingdom.
ATCC : American Type Culture Collection.
IMRU : Waksmans Institute of Microbiology, Rutgers University, New Brunswick, N.J., U.S.A.
NRRL : Northern Regional Research Laboratories, Peoria, ILL., U.S.A.
CGSC : E. coli Genetic Stock Center

TABLE 2

Plamids and Phages

| Designation | Relevant characteristics | Source of reference |
|---|---|---|
| pIJ702 | Thiostrepton resistance and melanine+ | 3 |
| pIJ699 | Thiostrepton, viomycin and Kanamycin resistances | 4 |
| pIJ61 | Thiostrepton and neomycin resistances | 5 |
| pIJ486 | Thiostrepton resistance and aph gene without promoter | 6 |
| pULAD series | Streptomyces and E. coli vectors carrying saf gene and/or adjacent sequences | This work |
| pIJ486::216 | pIJ486 carrying the saf promoter region | This work |
| pUC19 | bla+, lacZpZoZ' | 7 |
| pIJ2921 | bla+, lacZpZoZ' | See FIG. 10 |
| M13 mp10 and mp11 | Phages for generation of single-strained DNA | 8 |

REFERENCES QUOTED IN TABLES 1 AND 2

1. Hoffman, C. S., and A. Wright. 1985 Fusions of secreted proteins to alkaline phosphatase: an approach for studying protein secretion. Proc. Natl. Acad. Sci. USA 82:5107-5111.
2. Messing, J., R. Crea, and P. H. Seeburg. 1981. A system for shotgun DNA sequencing. Nucl. Acids. Res. 9:309-321.
3. Katz, E., C. J. Thompson, and D. A. Hopwood. 1983. Cloning and expression of the tyrosinase gene from Streptomyces antibioticus in Streptomyces lividans. J. Gen. Microbiol. 129:2703-2714.
4. Kieser, T., and R. E. Melton. 1988. Plasmid pIJ699, a multicopy positive-selection vector for Streptomyces. Gene 65:83-91.
5. Hopwood, D. A., M. J., Bibb, K. F. Chater, T. Kieser, C. J. Bruton, H. M. Kieser, D. J. Lydiate, C. P., Smith, J. M. Ward, and H. Schrempf. 1985. Genetic manipulation of Streptomyces. A Laboratory Manual. The John Innes Foundation, Norwich, U.K.
6. Ward, J. M., G. R. Janssen, T. Kieser, M. J. Bibb, M. J. Buttner, and M. J. Bibb. 1986. Construction and characterization of a serie of multi-copy promoter-probe plasmid vectors for Streptomyces using the aminoglycoside phosphotransferase gene from Tn5 as indicator. Mol. Gen. Genet. 203:468-478.
7. Yanisch-Perron, C., J. Vieira, and J. Messing. 1985. Improved M13 phage cloning vectors and host strains: mucleotide sequences of the M13mp18 and pUC19 vectors. Gene 33:103-119.
8. Messing, J. 1983.New M13 vectors for cloning. Methods Enzymol. 101:20-78.

What we claim is:

1. A substantially pure polypeptide having the following amino acid sequence:

Met Cys Ser Ala Val Val Ala Ala Ala Val Ser Ser Met Ser Arg
Arg Arg Arg Arg Ala Ser Ala Thr Arg Arg Ser Ala Ala Val Ser
Pro Pro His Thr Pro Tyr Gly Ser Gly Cys Ile Ser Ala Cys Ser
Trp His Ser Thr Ile Thr Gly His Arg Ala Gln Thr Arg Leu Ala
Ala Ser Ser Arg Ala Ser Arg Ala Ala Val Gly Ser Phe Asp Gly
Ala Lys Asn Arg Pro Ala Ser Ser Arg Arg Gln Ala Ala Ser Glu
Cys Gln Gly Pro Ala Ser Ser Ser Arg Ala Gly Val Arg Trp Ala
Gly Thr Ala Ala Asn Gly Arg Gly ter.

2. A substantially pure polypeptide which is the same as a polypeptide encoded by a DNA which hybridizes under stringent conditions with the following nucleotide sequence:

ATG TGC TCG GCC GTC GTC GCG GCG GCC GTG AGC TCG ATG TCC CGC
CGT CGC CGC CGG GCC AGC GCC ACC CGG CGC TCC GCT GCG GTG AGC
CCG CCC CAC ACT CCG TAC CGC TCG GGC TGT ACT AGC GCG TGC TCC
TGG CAC TCC ACC ATC ACC GGA CAC CGG GCA CAG ACC CGC TTG GCC
GCC TCC TCG CGG GCC AGC CGG GCG GCG GTC GGC TCC TTC GAC GGG
GCG AAG AAC AGG CCG GCC TCG TCG CGG CGG CAG GCC GCA TCG GAA
TGC CAG GGG CCC GCG TCG TCC TCC CGT GCG GGG GTC CGC TGG GCC
GGA ACG GCG GCG AAG AAC AGA GGC TGA and which has substantially the same activity in increasing production of extracellular enzymes as that of the polypeptide coded for by the nucleotide sequence set forth in this claim.

* * * * *